United States Patent
Hayre

(10) Patent No.: US 7,272,559 B1
(45) Date of Patent: Sep. 18, 2007

(54) NONINVASIVE DETECTION OF NEURO DISEASES

(75) Inventor: Harbhajan S. Hayre, Houston, TX (US)

(73) Assignee: CEIE specs, Inc., Houston, TX (US)

( * ) Notice: Subject to any disclaimer, the term of this patent is extended or adjusted under 35 U.S.C. 154(b) by 830 days.

(21) Appl. No.: 10/676,068

(22) Filed: Oct. 2, 2003

(51) Int. Cl.
G10L 15/08 (2006.01)

(52) U.S. Cl. .................. 704/236; 704/205; 704/209

(58) Field of Classification Search ............... 704/203, 704/205, 209, 204, 236, 207; 424/239.1
See application file for complete search history.

(56) References Cited

U.S. PATENT DOCUMENTS

| | | |
|---|---|---|
| 5,776,055 A | 7/1998 | Hayre |
| 5,839,445 A | 11/1998 | Kaufman |
| 5,840,018 A | 11/1998 | Michaeli |
| 5,855,550 A | 1/1999 | Lai et al. |
| 5,868,134 A | 2/1999 | Sugiyama et al. |

OTHER PUBLICATIONS

An Electronic Model of Brain Damaged Speech; Prof. H.S. Hayre, Electrical Eng'r Dept. and Dr. W.E. Fann, Chief Psychiatrist, Veterans Research Center, Houston, Texas; Proc. 24th Rocky Mtn. Bioeng. Symp., North Dokota State University, Fargo, I-, Apr. 27-28, 198-.*

Brain Cell Damange from Speech; Dr. Habbss. Hayre; Processings of DAGA 2001, Hamburg, Germany; Impairment Measures Inc. (Ltd. U.K.), P.O. Box 19756, Houston, Texas 77224-9756.

* cited by examiner

*Primary Examiner*—Huyen X. Vo
(74) *Attorney, Agent, or Firm*—Jones, Tullar & Cooper, P.C.

(57) ABSTRACT

Noninvasive, remote methods and apparatus for detecting early phases of neuro diseases such as the non-tremor phase of Parkinson's disease, dyskinesia, dyslexia and neuroatrophy, etc., are disclosed. Five words spoken either directly into a microphone connected to a local analysis system or remotely, as by way of a telephone link to a system for analysis of time and frequency domains of speech characteristics are representative of the presence of disease. The method includes the steps of transducing a set of unmodified spoken words or numbers into electrical signals which are bandlimited and amplified. These signals are analyzed in both time and frequency domains to detect and measure the manifestation of neurological disorders in the envelope of the time representation and spectral density of the words. Detection is carried out when the subject's body is in contact with neither a sensor nor an instrument, nor subjected to any other invasive means such as providing body fluids or breath, and without the need to perform any psychomotor functions.

11 Claims, 2 Drawing Sheets

Speech Signal – Time Domain

Speech Signal – Spectral Density

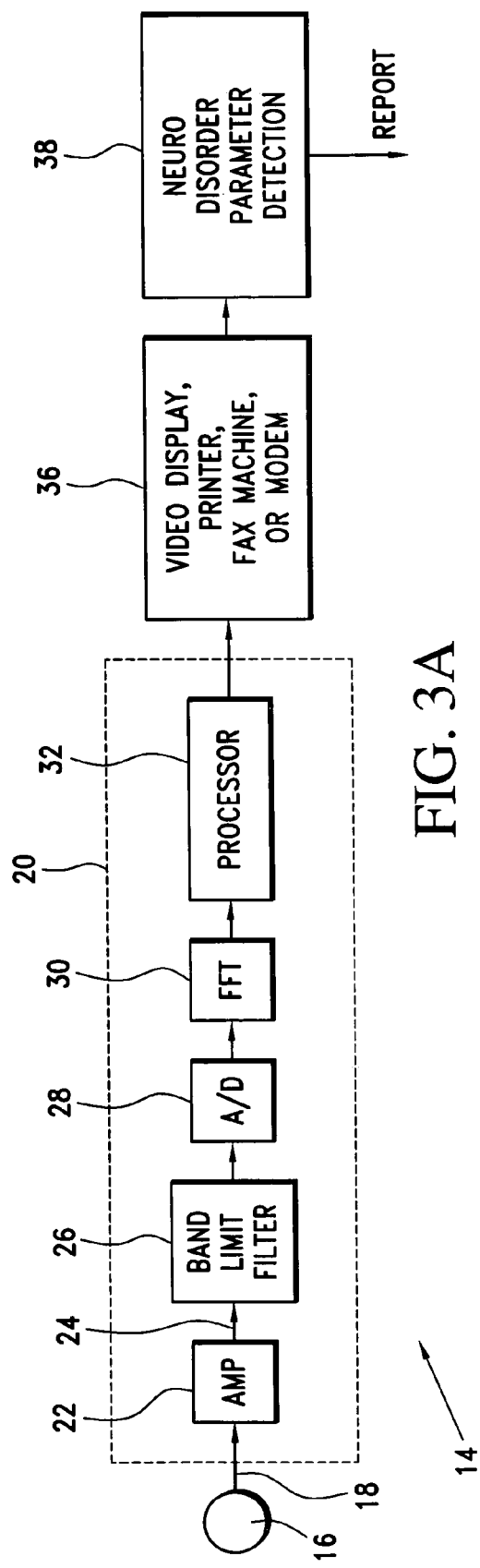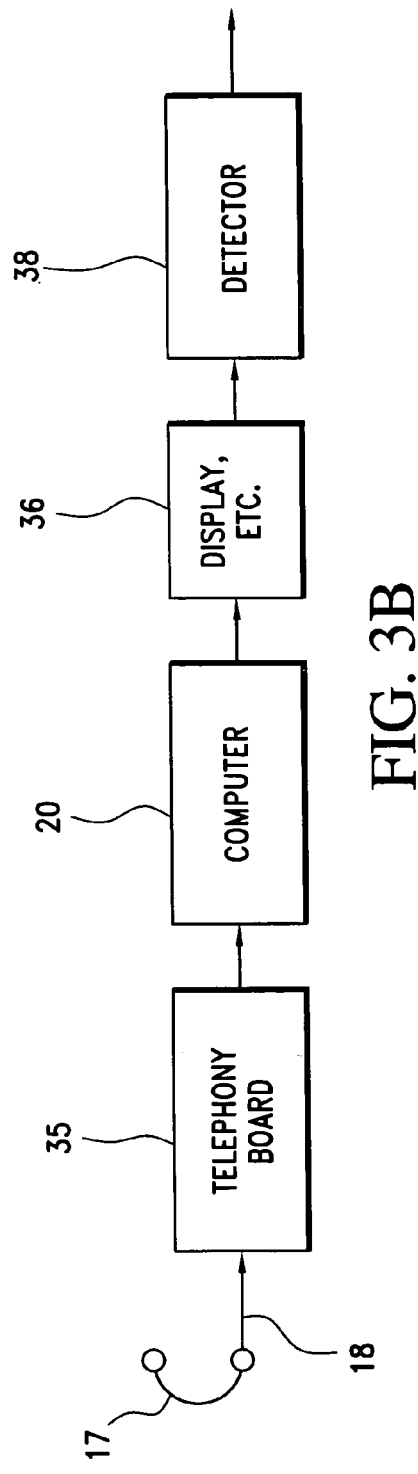

NONINVASIVE DETECTION OF NEURO DISEASES

BACKGROUND OF THE INVENTION

This invention relates to noninvasive, remote method and apparatus for detecting early phases of neuro diseases such as the non-tremor phase of Parkinson's disease, dyskinesia, dyslexia and neuroatrophy etc. etc. from five words spoken either directly into a microphone connected to a local analysis system or remotely, as by way of a telephone link to such a system for analysis of time and frequency domains of speech characteristics representative of the presence of disease.

The onset of Parkinson's, for example, may not exhibit any outward symptoms for up to ten years prior to the onset of involuntary, rhythmic shaking of a patient's hands, head or both. Other symptoms may include excessive salvation, and abdominal cramps. In the advanced stages of Parkinson's, memory and thought processes may also deteriorate. An early non-tremor phase detection of Parkinson's and other neuro diseases or neurodegeneration is desirable so that appropriate remedial medication may improve the quality of life for the patients as well as reduce the cost of healthcare both to the subject's families and to government and private health care systems.

Presently, no reliable pre-symptomatic diagnostic method or apparatus is known to exist. Furthermore, physicians find it difficult to distinguish Parkinson's from other neuro diseases in their early phases. Time consuming and expensive methods such as magnetic resonance imaging or body fluid analysis are neither completely effective nor economical.

Recently, researchers offered some evidence of a genetic link for late-onset Parkinson's disease. Some psychologists claim to identify Alzheimer with 80% success from touch tone telephone instructions such as "spell fun" and press "1" if a recorded sentence makes sense etc. Extensions of available diagnostic techniques occasionally help prediagnose neuro-dysfunctions other than Parkinson's. For instance, a male patient on Parkinson's medication was found to suffer from another neuro disorder, whereas a female patient on Parkinson's medication was found to suffer from extreme stress instead. Therefore, the need for accurate methods of detection of a variety of neurodiseases are badly needed.

Many inventors have claimed to noninvasively detect diseases while using body sensors, such as devices for diagnosing migraine headaches by monitoring the effective diameter of preselected blood vessels supplying blood to the brain. Similarly, the use of a retinal image to determine retinal disease and the use of a confocal microscope to observe diseases of finger nail, toe nail, and the skin or a mucus membrane have been described in the prior art. Remote monitoring of multiple medical parameters via RF signals from a patient attached to monitors is also known. However, there is no system or apparatus available to remotely and completely noninvasively, without any sensors attached to the body, detect the early phases of neuro diseases such as Parkinson's, neuro atrophy, dyskinesia, etc.

SUMMARY OF INVENTION

An objective of this invention is to provide a truly noninvasive, electronic, and remotely useable apparatus and method for detection and diagnosis of the early, non-tremor phase of Parkinson's disease, and other diseases such as neuro atrophy and neuro degradation, etc.

Another object of this invention is to utilize human speech, which is known to contain correlates of neurological disorders such as Parkinson's disease, Alzheimer, neural atrophy or neuro degradation, etc., in the detection of such disorders.

A further object is to provide a numerical indicator of the severity of neurological diseases, including Parkinson's disease.

A further object of this invention is to eliminate the need for having prior medical history or a baseline of a subject in order to detect and diagnose neurological disorders.

A further object is to provide telephone-based monitoring of a subject for the detection of neurobased diseases.

Speech involves nearly 67.5% of the cerebral/neurological centers of the brain and at least one hundred muscles and, therefore, is one of the most reliable body signals containing information about neuro-disorders. The nerve cells in certain of the Basal Ganglia of the brain (the Substatia Nigra, Locus Careruleus, the Globus Pallidus, and their afferent and efferent nerve connections) are subject to degeneration. It is further known that these neurological centers control movement, particularly semiautomatic movements such as swinging arms while walking. The deterioration of these nerve centers upsets the delicate balance between two body chemicals, dopamine and acetylchlorine, that are essential for controlling the transmission of nerve impulses within these parts of the nervous system. Parkinsonian symptoms are the result of the loss of such controls and coordination. Similarly, other neuro disorders affect coordination, memory, control, and cognitive functions. Even endocrinological disorders affect some of these cerebral subsystems, although medical educators treat neurological and endocrinological systems as two separate systems, even in the face of the fact that the cerebral system controls disorders in both systems. The forgoing forms the theoretical basis of the discovery that neuro disorders are manifested in speech signals, and certain parameters thereof are indicative of early phase onset of such disorders.

Briefly described, the method of this invention includes the steps of transducing a set of unmodified spoken words or numbers into electrical signals which are bandlimited and amplified. The band limiting is automatically accomplished when using a telephone for example, but a separate bandlimiting filter may be used to limit the speech to frequencies between 65 Hz and 3,000 Hz. These signals are analyzed in both time and frequency domains to detect diagnostic parameters for neuro disorders such as Parkinson's, among many other neuro diseases. For example, a subject may be asked to recite five words in sequences, such as one . . . one . . . two . . . eight . . . nine, into a microphone or into a telephone connected to a computer, and the speech signal is analyzed in both the time and frequency domains to detect and measure the manifestation of neurological disorders in the envelope of the time representation and spectral density of the words. Thus, the envelope of the spectrum of the word "one" of a neuro-normal individual resembles a bell shaped curve, whereas in the case of a person having Parkinson's disease, the envelope is distorted in a very unique manner indicated by a depression in its structure. Such a distortion may resemble the back of a two-humped camel. It is noted, however, that in the case of individuals with severe alcohol or drug damaged brain cells it may not be possible to easily detect these diagnostic parameters.

In accordance with the invention, therefore, detection is carried out when the subject's body is in contact with neither a sensor nor an instrument, nor subjected to any other invasive means such as requiring to provide body fluids or breath, and without the need to perform any psychomotor functions or Magnetic Resonance Imaging scans of brain or imaging thereof.

BRIEF DESCRIPTION OF DRAWINGS

The foregoing, and additional objects, features and advantages of the present invention will become apparent to those of skill in the art from the following detailed description of a preferred embodiment thereof, taken with the accompanying drawings, in which:

FIGS. 3A and 3B are block diagrams of a neurological impairment measurement apparatus for use in the present invention, FIG. 3A being in situ using a microphone, and FIG. 3B being remote by using a telephone.

DESCRIPTION OF PREFERRED EMBODIMENT

Figure 1:
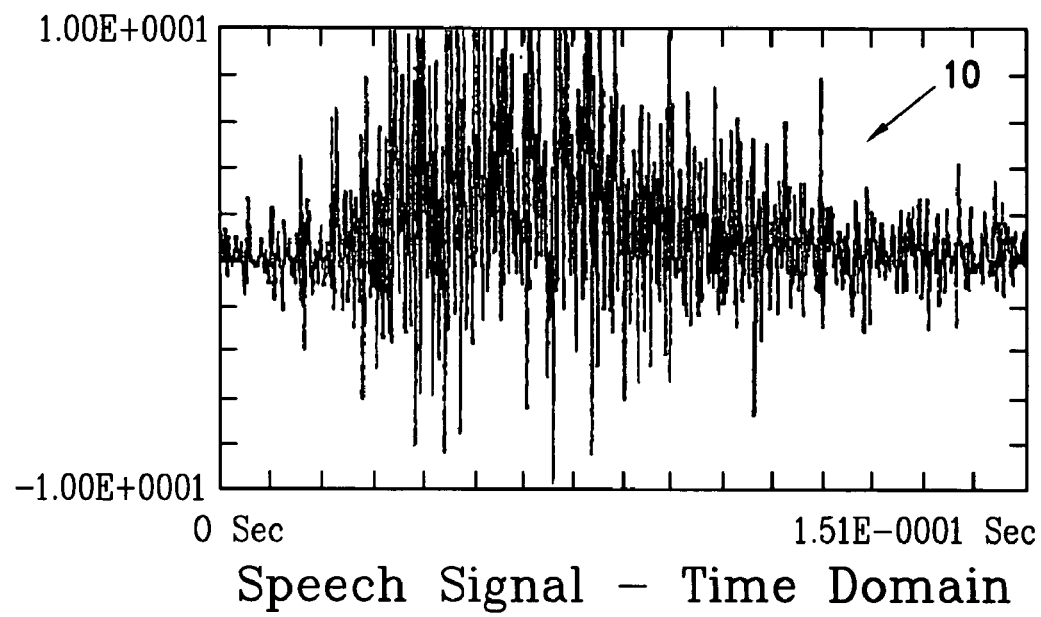
FIG. 1 is a graphical illustration of a speech signal time domain, showing time vs. amplitude.

Turning now to a more detailed description of the present invention, a preferred form of the method of the invention includes the steps of transducing a set of words spoken by a subject to be tested into electrical signals, such speech signals producing typical wave patterns, such as those illustrated at 10 in FIG. 1. The signals are amplified, frequency band limited, converted to digital signals, and are Fast Fourier Transformed (FFT) to obtain the frequency spectra of the speech. A typical spectrum is illustrated by waveform 12 in FIG. 2.

The processing of the received and transduced speech signals may be carried out in the neurological disorder detector apparatus 14 illustrated in FIGS. 3A and 3B. As illustrated, a microphone 16 (FIG. 3A) such as a Radio Shack model 33-985, or a digital microphone such as that provided by Analog Devices, Inc., or the equivalent, or a telephone 17 (FIG. 3B) is used to transduce spoken words into their corresponding electrical signals which are supplied by way of line 18 to suitable signal processing equipment indicated at 20. Such equipment may be a commercially available personal computer such as a 386DX30 or any newer computers, including suitable audio processing boards.

The processor 20 preferably includes an amplifier 22 for receiving audio signals on line 18 with the amplified signals being applied by way of line 24 to a band pass filter 26. Such a filter may be an antialiasing filter such as "Tahiti" model personal computer board available from Turtle Beach Systems, Inc., which filters and digitizes the audio signals as indicated by the analog to digital circuit 28. The digitized signals are then Fast Fourier Transformed (FFT) as indicated at FFT block 30, and the resulting signal is processed in processor 32 of computer 20, utilizing commercially available digital signal processing software, such as a Spectra Plus 3.0" available from Pioneer Hill Software, Inc., to produce the power spectral density signals 12 of FIG. 2 on output line 34. The same process and functions can be carried out using telephone 17 to call to the personal computer 20, as illustrated in FIG. 3B, incorporating a computer telephony Interactive Voice Response board 35, such as that available form COPIA INTERNATIONAL and the Fast Fourier Transform Software as identified in FIG. 3A.

The basic equation for determining the power spectral density is as follows:

$$S(f_k) = \left[(1/N)\sum_{n=0}^{N-1} x(t_n)\exp(-jw_k t_n)\right]^2 \quad (\text{Eq. 1})$$

Where:
$S(f_k)$=power spectral density
$W_k = kW_o = 2\pi f_o k$
$t_n$=Time location of $n^{th}$ sample of $x(t)$ $$T_o = \text{Sampling period} = \frac{1}{f_o}$$

N=Total number of samples

The function $x(t_n\text{-}nT_o)$ is an n-point sequence of digitized speech that is T seconds in length. In the case of Discrete Fourier Transformation, the function x(f) becomes:

$$x(f_k) = 1/N \sum_{n=0}^{N-1} x(nT_o)\exp(-j2\pi kn/N) \quad (\text{Eq. 2})$$

and its power spectral density is defined as:

$$S(f_k) = |x(f_k)|^2 \quad (\text{Eq. 3})$$

The power spectral density $S(f_k)$ is converted into decibels (db), and smoothed with 2-6 db smoothing window. It is then processed to obtain its envelope and its envelope peaks and nulls, and is sent to a printer 36 or is stored for additional analysis to detect various neuro-disorders parameters.

The value of the measurement is supplied by way of line 34 to display or storage unit 36 such as a printer, a FAX machine, a modem, or the like, which allows the value to be displayed, printer or stored for future use, or sent to a remote location over a communication link. For example, the computer 64 may incorporate a FAX modem which will transmit the measurement to a remote computer or FAX machine by way of any commercially available communication link.

Figure 2:
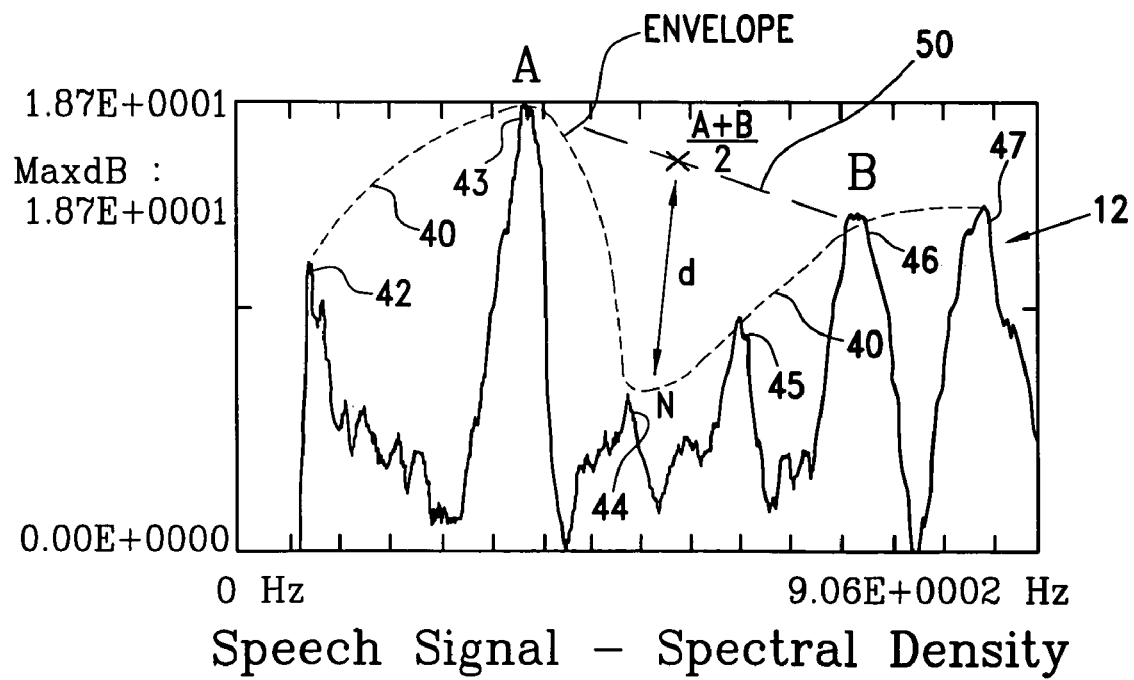
FIG. 2 is a graphical illustration of a speech signal frequency spectrum showing spectral density vs. frequency.

As illustrated in FIG. 2, the spectral density signals 12 are included in an envelope 40 which tracks the speech frequency peaks 42, 43, . . . 47 . . . , in the first formant in the frequency domain 65 Hz to 3,000 Hz. Between successive maximum peaks 43 and 46, labelled "A" and "B", respectively, the envelope 40 dips below the average amplitude, in decibels, of peaks A and B, indicated at long-dashed line 50, by an amount "d", above the null, labelled N and indicated at peak 44 in FIG. 2.

These maximum peaks on opposite sides of a minimum point generally occur only one in the spectrum, so are readily identifiable. The relationship of a depression in the envelope 40 to the average value (A+B)/2 of the highest peaks on either side of the depression indicated by line 50 can be used, in accordance with the invention, to determine a Parkinson's Severity Index (SI) which indicates a measure of the progression of this disease as a percentage of fully developed Parkinson's. The ratio of the amplitude, in decibels (db) of the depression d to the average level of the adjoining shoulder peaks on both sides of the depression (A+B)/2, is multiplied by a constant-K, so that:

$$SI = 2d\,K/(A+B) \quad (\text{Eq. 5})$$

Small depressions, of less than the maximum db smoothing levels, which may lie between 2 to 6 db for example, are not used in this calculation. Lower values of Si may indicate early phase Parkinson's, whereas large values are indicative of an advanced stage thereof.

Similarly, dyskinesia is indicated by an almost linear decay of the power spectral density in the upper half of the frequency range of the first formant. Brain cell damage by excessive alcohol or drug abuse distorts the spectral density of the first formant into a single peak instead of a normal multi-harmonic spectra. The location of the single peak is determined by the chemical abused. Neuropathy is represented by a null near the middle of the first formant spectral density, and its envelope resembles a two hump camel top with a dip at lower end of spectrum. Some neuro disorders cause complete disappearance of certain harmonics in the spectral density. Neurologists in general have problems distinguishing between various neuro disorders, since they tend to go over a check list of symptoms to identify these, and many symptoms are not necessarily limited only to a single neuro disorder. There are other unique spectrum distortions attributed to other neuro disorders, such as, but not limited to, missing a particular harmonic, attenuation of the magnitude of the said spectrum, and distortion of a section of spectrum, including numerous parameters of disorders represented by combinations of nearly 6,000 bits of information in the band limited speech signal as described above. Simply described, maximas, minimas, up and down slopes of all the harmonics, high frequency jitter riding on the up and down slopes of each harmonic, and various combinations thereof have been identified by this invention to represent endocronological, physical, and psychological parameters, and there exist numerous other combinations which identify other and endocron types of disorders. which can also be detected in this manner.

It will be understood that variations and modifications of the invention as described herein may be made without departing from the true spirit and scope of the invention as set out in the accompanying claims.

What is claimed is:

1. A noninvasive method of identifying and measuring a neurological manifestation in human speech of an early phase of neuro disease including:
    converting a human subject's spoken words into corresponding electrical signals;
    amplifying said electrical signals;
    frequency band limiting, and signal conditioning the said electrical signals to produce modified signals;
    determining an envelope of said modified signals;
    determining a spectral density of said modified signals and providing a spectral density signal;
    smoothing said spectral density signal;
    determining a spectral envelope of said smoothed spectral density signal;
    determining the presence of a depression in said spectral envelope;
    determining an amplitude of said depression with reference to an average db level of two shoulder peaks in said spectral density signal on either side of said depression;
    determining a ratio of said amplitudes of said depression and said average db level of said two shoulder peaks; and
    using said ratio for identifying and measuring a neurological manifestation in the subject's spoken word, of early phases of neuro disease.

2. The method of claim 1, further including multiplying said ratio by a constant k to obtain a Parkinson Severity Index.

3. The method of claim 2, further including separating Parkinson's disease from said neuro disorders, by using different constants than those of Parkinson.

4. The method of claim 1, further including determining a compressed range for said Parkinson Severity Index by selecting a narrow bandwidth corresponding to a first format of said electrical signals.

5. The method of claim 1, further including converting said spoken words using telephony computer boards.

6. The method of claim 1, further including detecting parameters corresponding to Parkinson neuro disorders.

7. The method of claim 1, further including using said ratio and providing prediagnostic assistance to a physician for use in treating said neuro disease.

8. The method of claim 1, further including using said ratio and detecting brain cell damage.

9. The method of claim 1, further including using said ratio and detecting dykinesia.

10. The method of claim 1, further including using said ratio and detecting neuro atrophy.

11. The method of claim 1, further including using said ratio and detecting neuropathy.

* * * * *